United States Patent [19]

Fujiwara et al.

[11] Patent Number: 4,503,271

[45] Date of Patent: Mar. 5, 1985

[54] PROCESS FOR THE PRODUCTION OF PARA-VINYL PHENOL BY DEHYDROGENATION OF PARA-ETHYL PHENOL

[75] Inventors: Hiroshi Fujiwara; Hatsutaro Yamazaki, both of Saitama; Kazuo Ozawa, Ibaraki, all of Japan

[73] Assignee: Maruzen Oil Co., Ltd., Osaka, Japan

[21] Appl. No.: 528,839

[22] Filed: Sep. 2, 1983

[30] Foreign Application Priority Data

Jun. 15, 1983 [JP] Japan ................................. 58-107262

[51] Int. Cl.³ ....................... C07C 37/00; C07C 39/19
[52] U.S. Cl. .................................. 568/799; 568/740; 568/782
[58] Field of Search ........................ 568/799, 782, 740

[56] References Cited

U.S. PATENT DOCUMENTS 4,346,249  8/1982  Krabbenhoft ....................... 568/782

Primary Examiner—Werren B. Lone
Attorney, Agent, or Firm—Sughrue, Mion, Zinn, Macpeak and Seas

[57] ABSTRACT

A process for the production of p-vinyl phenol by the dehydrogenation of p-ethyl phenol in a gaseous phase in the presence of a catalyst and a diluent wherein the dehydrogenation of p-ethyl phenol is effected with phenol and/or p-cresol being present in the reaction system in an amount of 5 to 50 wt % of the amount of p-ethyl phenol.

11 Claims, 3 Drawing Figures

PROCESS FOR THE PRODUCTION OF PARA-VINYL PHENOL BY DEHYDROGENATION OF PARA-ETHYL PHENOL

FIELD OF THE INVENTION

The present invention relates to a process for the production of p-vinyl phenol by the dehydrogenation of p-ethyl phenol. More specifically, the present invention relates to a process for the production of p-vinyl phenol at an increased selectivity by the catalytic dehydrogenation of p-ethyl phenol in a gaseous phase in the presence of a diluent.

BACKGROUND OF THE INVENTION

Methods for producing vinyl phenols from ethyl phenols by their catalytic dehydrogenation in a gaseous phase in the presence of water, benzene or some other diluent such as nitrogen or carbon dioxide gas are known and are described in Japanese Patent Publication Nos. 41183/74 and 43491/78, as well as in Japanese patent application (OPI) Nos. 55529/79, 28958/80 and 203022/82, etc. (The symbol OPI as used herein means an unexamined published Japanese patent application).

In the above known methods, the selectivity for the end product p-vinyl phenol can be increased up to 90 to 95% or higher by employing optimum reaction conditions. However, in industrial operations using large apparatuses, for example, a large fixed bed catalytic reactor, the dehydrogenation of p-ethyl phenol, which is an endothermic reaction, causes fluctuations in the temperature of the catalyst bed or the reactant flow through the catalyst bed. As a result, it has been difficult to maintain optimum conditions throughout the reaction system in industrial operations and the selectivity for p-vinyl phenol has been at most only 80 to 85%.

In addition, the cost of p-ethyl phenol accounts in large part for the overall cost of the production of p-vinyl phenol. Thus, reduction of the loss of p-ethyl phenol, which occurs in industrial operations due to side reactions, has long been desired.

SUMMARY OF THE INVENTION

Therefore, various studies have been conducted in order to develop a method for increasing the selectivity for p-vinyl phenol in industrial operations using a large reactor. As a result of these studies, it has been found that the selectivity for p-vinyl phenol can be increased by incorporating a certain amount of phenol and/or p-cresol in the dehydrogenation system.

In the dehydrogenation of p-ethyl phenol, phenol or p-cresol from which an alkyl group has been eliminated, and benzene, toluene or ethyl-benzene from which a hydroxyl group has been removed, are produced as by-products. However, by incorporating a certain amount of phenol and/or p-cresol in the reaction system, the side reactions that give rise to these by-products are inhibited and the selectivity for the end product, i.e., p-vinyl phenol, is increased. This effect is increased as more phenol and/or p-cresol is present in the reaction system. However, the percent conversion from p-ethyl phenol is decreased and the yield of p-vinyl phenol is lowered when too much phenol and/or p-cresol is used. Therefore, the amount of phenol and/or p-cresol should not exceed the level beyond which the percent conversion from p-ethyl phenol is reduced. In short, it has been determined that by holding the amount of phenol and/or p-cresol within a certain range, the selectivity for p-vinyl phenol is increased to an extent that compensates for the decrease in the percent conversion from p-ethyl phenol. As a result, the yield of p-vinyl phenol is increased.

One object of the present invention is to provide a process for converting p-ethyl phenol to p-vinyl phenol which is highly selective for p-vinyl phenol.

Another object of the present invention is to provide an industrial process using a large reactor for converting p-ethyl phenol to p-vinyl phenol which is highly selective for p-vinyl phenol.

Still another object of the present invention is to provide an industrial process for producing p-vinyl phenol with a minimum loss of p-ethyl phenol.

The present invention provides a process for the production of p-vinyl phenol by the dehydrogenation of p-ethyl phenol in a gaseous phase in the presence of (a) a catalyst; (b) a diluent; and (c) 5 to 50 wt% of phenol and/or p-cresol based on the amount of p-ethyl phenol.

According to the process of the present invention, p-vinyl phenol can be produced from p-ethyl phenol on an industrial scale with the selectivity for the end product being higher than that achieved in the conventional art and with a reduction in the loss of the starting material due to side reactions.

Furthermore, according to the present invention, the yield of the end product per pass of the starting material through the reaction system is equal to or higher than that conventionally achieved.

In addition, since the selectivity for p-vinyl phenol is high in the process of the present invention than in conventional processes, by recycling the unreacted portion of p-ethyl phenol to the reaction system a number of times, the loss of p-ethyl phenol due to the undesired side reactions can be minimized and almost all of the starting material can be converted to p-vinyl phenol.

DETAILED DESCRIPTION OF THE INVENTION

Figure 1B:
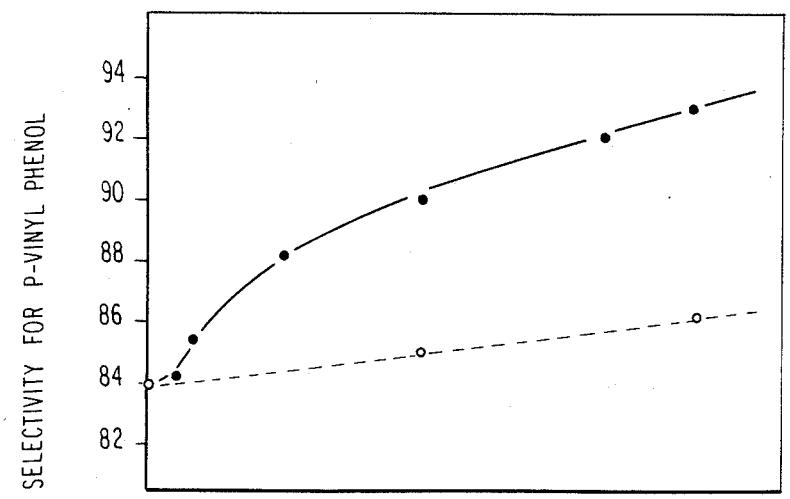
FIG. 1(b) illustrates the selectivity for p-vinyl phenol as obtained in Examples 1 to 4 and Comparative Examples 1 to 5.

In the process of the present invention, dehydrogenation of p-ethyl phenol is performed in a reaction system containing 5 to 50 wt%, preferably 7 to 40 wt%, of phenol and/or p-cresol based on the amount of p-ethyl phenol. If the amount of phenol and/or p-cresol is less than 5 wt%, inhibition of the undesired side reactions is not sufficient to achieve the intended high selectivity for p-vinyl phenol.

In the conventional dehydrogenation process for the production of p-vinyl phenol from p-ethyl phenol, the starting material sometimes contains up to 2-3 wt% of phenol and p-cresol as impurities. However, such small amounts do not inhibit the occurrence of the undesired side reactions.

If the amount of phenol and/or p-cresol exceeds 50 wt%, the time of contact between p-ethyl phenol and the catalyst is shortened to such an extent that the percent conversion from p-ethyl phenol is greatly reduced or the yield of p-vinyl phenol per pass of p-ethyl phenol through the reaction is lowered.

The yield of the end product per pass of p-ethyl phenol through the reaction depends on the balance between the increase in the selectivity for p-vinyl phenol and the decrease in the percent conversion from p-ethyl phenol. This balance in turn depends on the reaction conditions. If the reaction system contains 5 to 50 wt% of phenol and/or p-cresol based on the amount of p-ethyl phenol, the increase in the selectivity for p-vinyl phenol is equal to or more than the decrease in the percent conversion from p-ethyl phenol. Further, the yield of the end product is the same as or more than that achieved in conventional methods.

In the process of the present invention, either phenol or p-cresol or both may be added to the reaction system, but better results are obtained by using a mixture of both compounds. Preferably, phenol and p-cresol should be present in a weight ratio of 1:0.5 to 1:5, with the weight ratio of 1:1 to 1:3 particularly preferred.

The phenol and/or p-cresol is preferably added to the starting material p-ethyl phenol before it is supplied to the reactor. Alternatively, the phenol and/or p-cresol may be added to the reaction system separately from the p-ethyl phenol. Phenol and/or p-cresol may be externally added to the p-ethyl phenol or they may be carried over from the step of preparing the p-ethyl phenol. For instance, if the p-ethyl phenol is pure enough to be substantially free of phenol and/or p-cresol, phenol and/or p-cresol is externally added in an amount from 5 to 50 wt% of the amount of p-ethyl phenol. If the p-ethyl phenol contains 2–3 wt% of phenol and/or p-cresol as impurities, additional phenol and/or p-cresol are added so that the summation of the impurities and the externally added phenol and/or p-cresol is from 5 to 50 wt% of the amount of p-ethyl phenol.

In the process of the present invention, the unreacted p-ethyl phenol may be recycled to the reaction system. Further, if the unreacted p-ethyl phenol contains 5 to 50 wt% of phenol and/or p-cresol, it may be immediately used as the starting material for the process of the present invention, i.e., without adding external phenol and/or p-cresol. On the other hand, if the unreacted p-ethyl phenol contains more than 50 wt% of phenol and/or p-cresol, it may be slightly purified to bring the content of phenol and/or p-cresol within the prescribed range. Note, p-ethyl phenol does not have to be highly purified to render it substantially free of these impurities. Therefore, one advantage of the process of the present invention is that the starting material need not be highly purified p-ethyl phenol such that it is substantially free of phenol and/or p-cresol.

According to the present invention, dehydrogenation of p-ethyl phenol is effected by bringing it into contact with a conventional dehydrogenation catalyst in a gaseous phase in the presence of 5 to 50 wt% of phenol and/or p-cresol using a common diluent. Any diluent and dehydrogenation catalyst may be used under any temperature and reaction conditions so long as the dehydrogenation of p-ethyl phenol is effected smoothly.

Diluents which can be used in the present invention include: (a) water; (b) hydrocarbons such as benzene, toluene, xylene and low-boiling point petroleum fractions; (c) inorganic gases such as carbon monoxide, carbon dioxide, nitrogen, helium and argon; and (d) mixtures thereof. Water (water vapor), benzene and toluene are preferred diluents. The diluents are used in an amount of 2 to 200 mols, preferably 3 to 20 mols, per mol of p-ethyl phenol.

Dehydrogenation catalysts which can be used in the present invention include: (a) iron oxides optionally supported on alkaline earth metal oxides as described in Japanese Patent Publication No. 43491/78; (b) an oxide of at least one metal selected from the group consisting of vanadium, molybdenum, manganese, cobalt, nickel, copper, zinc, cadmium, antimony, tellurium and cerium which is optionally supported on alkaline earth metal oxides as described in Japanese Patent Publication No. 41183/74; (c) chromium (III) oxide optionally combined with at least one metal oxide selected from the group consisting of zinc oxide, manganese oxide, titanium oxide and zirconium oxide as described in Japanese Patent Application (OPI) No. 55529/79; (d) tin (IV) oxide optionally combined with metallic tin powder or at least one metal oxide selected from the group consisting of magnesium oxide, chromium (III) oxide, zinc oxide and manganese (IV) oxide as described in Japanese Patent Application (OPI) No. 28958/80; (e) titanium (IV) oxide optionally combined with at least one metal oxide selected from the group consisting of manganese oxide, iron oxide, copper oxide, zinc oxide, zirconium oxide, molybdenum oxide, tin oxide, antimony oxide, cerium oxide, lithium oxide, magnesium oxide, calcium oxide and barium oxide as described in Japanese Patent Application (OPI) No. 203022/82; and various other known catalysts for dehydrogenating ethyl phenol into vinyl phenol.

Other usable catalysts include: oxides containing barium and tin which are optionally combined with at least one metal oxide selected from the group consisting of vanadium oxide, manganese oxide, iron oxide, copper oxide, zinc oxide, zirconium oxide, molybdenum oxide, antimony oxide, bismuth oxide and cerium oxide. When using such catalysts, the barium- and tin-containing oxide may be a mixture of barium oxide and tin oxide, or it may be in the form of a complex oxide such as barium stannate. The atomic ratio of barium to tin in the barium- and tin-containing oxide is from about 0.03:1 to 10:1, preferably from about 0.05:1 to 2:1. In addition, part of the barium in the oxide may assume a form other than barium oxide, such as barium peroxide or barium carbonate.

When the barium- and tin-containing oxide is combined with one of the metal oxides listed above, the mixing ratio is not limited to any particular value, but generally the atomic ratio of (Ba+Sn) to another metal is from about 0.01:1 to 100:1, preferably from about 0.1:1 to 10:1.

The above-listed metal oxides that can be used as dehydrogenation catalysts in the present invention may be prepared by any method. An example of such a method is to bake organic salts, organometallic compounds, or inorganic salts (e.g., hydroxides, carbonates, nitrates and halides) of the metals listed. In another example of such a method, a basic compound such as ammonia, caustic soda or caustic potash is added to aqueous solutions of inorganic or organic salts of these metals, the resulting precipitate is filtered, washed, dried and baked. Of course, the metal oxides listed above may be available as commercial products. Combinations of certain metal oxides with other metal oxides may also be prepared by any known method such as mixing, immersion or co-precipitation.

The above-identified metal oxides or combinations of certain metal oxides with other metal oxides may be immediately used as dehydrogenation catalysts after they are sized or their particles may be pressed into tablets or extrusion-molded into the desired shape.

The metal oxides or combinations of certain metal oxides with other metal oxides may be supported on carriers as required. Suitable carriers are inert carriers such as α-alumina, silicon carbide and diato-maceous earth. Active carriers such as γ-alumina and silica should not be used since they increase the chance of side reactions, e.g., the dealkylation, the polymerization or the deposition of carbonaceous material.

The process of the present invention is carried out at a reaction temperature between 400° and 700° C., preferably between 500° and 600° C. The reaction pressure may be subatmospheric, atmospheric or superatmospheric. Atmospheric pressure is generally preferred.

The supply rate of the starting material p-ethyl phenol is between 0.1 and $5^{-hr}$, preferably between 0.2 and $2.0^{-hr}$ in terms of the liquid hourly space velocity (LHSV).

After the dehydrogenation of p-ethyl phenol, the end product p-vinyl phenol is recovered from the reaction product and the residual fraction containing the unreacted p-ethyl phenol is recycled either immediately or after adjusting the content of phenol and/or p-cresol to be within the range of 5 to 50 wt% of the amount of p-ethyl phenol as the starting material for the next cycle of dehydrogenation. The end product p-vinyl phenol may be recovered from the reaction product by any method. One example is to recover the p-vinyl phenol as a polymerized product, i.e., the reaction product is first subjected to a polymerization step to polymerize the p-vinyl phenol and the resulting polymer is separated from the fraction containing the unreacted p-ethyl phenol by distillation or any other suitable technique.

The present invention is described in greater detail by reference to the following examples and comparative examples. It should be understood that these examples are presented for illustrative purposes only and are by no means intended to limit the scope of the invention. Unless otherwise specified, all "parts" and "percents" used in these examples and comparative examples are by weight.

EXAMPLE 1

A mixture of p-ethyl phenol (100 parts) with phenol (2 parts) and p-cresol (3 parts) was fed into a dehydrogenation reactor together with 10 mols of water per mol of p-ethyl phenol at 550°–580° C. under atmospheric pressure. The reactor was packed with 170 liters of tin (IV) oxide catalyst and p-ethyl phenol was supplied at a LHSV of $0.7^{-hr}$ for 36 hours. The resulting product was cooled to room temperature to obtain an oil phase in an amount of 112% of the p-ethyl phenol feed and an aqueous phase in an amount of 135% of the p-ethyl phenol feed. The oil phase was composed of 2.8% of phenol, 4.0% of p-cresol, 26.1% of p-vinyl phenol, 0.4% of a low-molecular weight polymer of p-vinyl phenol, 0.4% of an unknown substance, 58.3% of unreacted p-ethyl phenol and 8.0% of water. The aqueous phase was composed of 0.1% of phenol, 0.1% of p-cresol, 0.3% of p-vinyl phenol, 0.5% of p-ethyl phenol and balance of water. Therefore, the percent conversion from p-ethyl phenol was 34.5%, the selectivity for p-vinyl phenol was 85.5%, and the yield of p-vinyl phenol was 29.5%.

EXAMPLE 2

Dehydrogenation of p-ethyl phenol was effected as in Example 1 except that 5 parts of phenol and 10 parts of p-cresol were added to 100 parts of p-ethyl phenol. An oil phase and an aqueous phase were obtained in an amount of 122% and 134% of the p-ethyl phenol feed, respectively. The oil phase was composed of 4.7% of phenol, 8.9% of p-cresol, 23.9% of p-vinyl phenol, 0.2% of a low-molecular weight polymer of p-vinyl phenol, 0.4% of an unknown substance, 53.6% of unreacted p-ethyl phenol, and 8.3% of water. The aqueous phase was composed of 0.2% of phenol, 0.2% of p-cresol, 0.4% of p-vinyl phenol, 0.5% of p-ethyl phenol and balance of water. Therefore, the percent conversion from p-ethyl phenol was 33.7%, the selectivity for p-vinyl phenol was 88.2%, and the yield of p-vinyl phenol was 29.7%.

EXAMPLE 3

Dehydrogenation of p-ethyl phenol was effected as in Example 1 except that 10 parts of phenol and 20 parts of p-cresol were added to 100 parts of p-ethyl phenol. An oil phase and an aqueous phase were obtained in an amount of 139% and 133% of the p-ethyl phenol feed, respectively. The oil phase was composed of 7.3% of phenol, 14.7% of p-cresol, 20.8% of p-vinyl phenol, 0.2% of a low-molecular weight polymer of p-vinyl phenol, 0.4% of an unknown substance, 47.9% of unreacted p-ethyl phenol and 8.7% of water. The aqueous phase was composed of 0.3% of phenol, 0.3% of p-cresol, 0.4% of p-vinyl phenol, 0.5% of p-ethyl phenol and balance of water. Therefore, the percent conversion from p-ethyl phenol was 32.8%, the selectivity for p-vinyl phenol was 90.0%, and the yield of p-vinyl phenol was 29.5%.

EXAMPLE 4

Dehydrogenation of p-ethyl phenol was effected as in Example 1 except that 17 parts of phenol and 33 parts of p-cresol were added to 100 parts of p-ethyl phenol. An oil phase and an aqueous phase were obtained in an amount of 160% and 132% of p-ethyl phenol feed, respectively. The oil phase was composed of 10.5% of phenol, 20.8% of p-cresol, 17.9% of p-vinyl phenol, 0.2% of a low-molecular weight polymer of p-vinyl phenol, 0.3% of an unknown substance, 42.3% of unreacted p-ethyl phenol and 8.0% of water. The aqueous phase was composed of 0.4% of phenol, 0.4% of p-cresol, 0.4% of p-vinyl phenol, 0.5% of p-ethyl phenol and balance of water. Therefore, the percent conversion from p-ethyl phenol was 31.7%, the selectivity for p-vinyl phenol was 92.1%, and the yield of p-vinyl phenol was 29.2%.

COMPARATIVE EXAMPLE 1

Dehydrogenation of p-ethyl phenol was effected as in Example 1 except that neither phenol nor p-cresol was added to the p-ethyl phenol. An oil phase and an aqueous phase were obtained in an amount of 108% and 135% of the p-ethyl phenol feed, respectively. The oil phase was composed of 1.2% of phenol, 1.9% of p-cresol, 26.8% of p-vinyl phenol, 0.5% of a low-molecular weight polymer of p-vinyl phenol, 0.5% of an unknown substance, 59.7% of unreacted p-ethyl phenol, and 9.4% of water. The aqueous phase was composed of 0.1% of phenol, 0.1% of p-cresol, 0.3% of p-vinyl phenol, 0.4% of p-ethyl phenol and balance of water.

Therefore, the percent conversion from p-ethyl phenol was 35.0%, the selectivity for p-vinyl phenol was 83.9%, and the yield of p-vinyl phenol was 29.3%.

COMPARATIVE EXAMPLE 2

Dehydrogenation of p-ethyl phenol was effected as in Example 1 except that 1 part of phenol and 2 parts of p-cresol were added to 100 parts of p-ethyl phenol. An oil phase and an aqueous phase were obtained in an amount of 111% and 135% of the p-ethyl phenol feed, respectively. The oil phase was composed of 2.1% of phenol, 3.6% of p-cresol, 26.1% of p-vinyl phenol, 0.4% of a low-molecular weight polymer of p-vinyl phenol, 0.4% of an unknown substance, 58.3% of unreacted p-ethyl phenol and 9.1% of water. The aqueous phase was composed of 0.1% of phenol, 0.1% of p-cresol, 0.3% of p-vinyl phenol, 0.4% of p-ethyl phenol and balance of water. Therefore, the percent conversion from p-ethyl phenol was 34.8%, the selectivity for p-vinyl phenol was 84.1%, and the yield of p-vinyl phenol was 29.3%.

COMPARATIVE EXAMPLE 3

Dehydrogenation of p-ethyl phenol was effected as in Example 1 except that 20 parts of phenol and 40 parts of p-cresol were added to 100 parts of p-ethyl phenol. An oil phase and an aqueous phase were obtained in an amount of 172% and 131% of the p-ethyl phenol feed, respectively. The oil phase was composed of 11.5% of phenol, 23.2% of p-cresol, 16.4% of p-vinyl phenol, 0.1% of a low-molecular weight polymer of p-vinyl phenol, 0.3% of an unknown substance, 40.0% of unreacted p-ethyl phenol and 8.5% of water. The aqueous phase was composed of 0.5% of phenol, 0.5% of p-cresol, 0.3% of p-vinyl phenol, 0.4% of p-ethyl phenol and balance of water. Therefore, the percent conversion from p-ethyl phenol was 30.8%, the selectivity for p-vinyl phenol was 93.0% and the yield of p-vinyl phenol was 28.6%.

COMPARATIVE EXAMPLE 4

Dehydrogenation of p-ethyl phenol was effected as in Example 1 except that the phenol and p-cresol were replaced by an additional 30 parts of water to increase the amount of water to about 11.4 mols per mol of the p-ethyl phenol. An oil phase and an aqueous phase were obtained in an amount of 107% and 165% of the p-ethyl phenol feed, respectively. The oil phase was composed of 1.1% of phenol, 1.7% of p-cresol, 26.4% of p-vinyl phenol, 0.3% of a low-molecular weight polymer of p-vinyl phenol, 0.7% of an unknown substance, 60.8% of unreacted p-ethyl phenol and 9.0% of water. The aqueous phase was composed of 0.1% of phenol, 0.1% of p-cresol, 0.3% of p-vinyl phenol, 0.4% of p-ethyl phenol and balance of water. Therefore, the percent conversion from p-ethyl phenol was 34.0%, the selectivity for p-vinyl phenol was 85.0%, and the yield of p-vinyl phenol was 28.9%.

COMPARATIVE EXAMPLE 5

Dehydrogenation of p-ethyl phenol was effected as in Example 1 except that the phenol and p-cresol were replaced by an additional 60 parts of water to increase the amount of water to about 14.1 mols per mol of the p-ethyl phenol. An oil phase and an aqueous phase were obtained in an amount of 107% and 194% of the p-ethyl phenol feed, respectively. The oil phase was composed of 1.0% of phenol, 1.4% of p-cresol, 25.9% of p-vinyl phenol, 0.2% of a low-molecular weight polymer of p-vinyl phenol, 0.7% of an unknown substance, 61.8% of unreacted p-ethyl phenol and 9.0% of water. The aqueous phase was composed of 0.1% of phenol, 0.1% of p-cresol, 0.3% of p-vinyl phenol, 0.4% of p-ethyl phenol and balacne of water. Therefore, the percent conversion from p-ethyl phenol was 33.0%, the selectivity for p-vinyl phenol was 86.2%, and the yield of p-vinyl phenol was 28.4%.

Figure 1A:
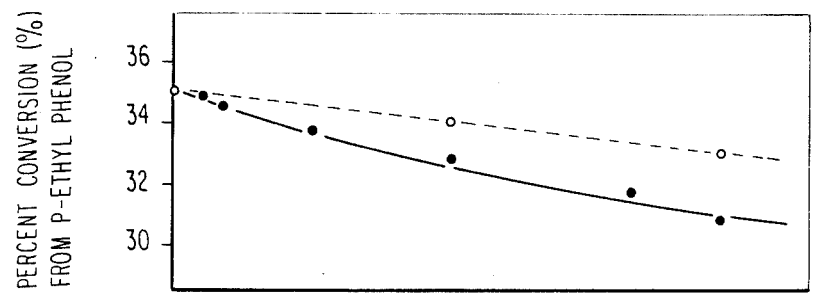
FIG. 1(a) illustrates the percent conversion from p-ethyl phenol as obtained in Examples 1 to 4 and Comparative Examples 1 to 5.
Figure 1C:
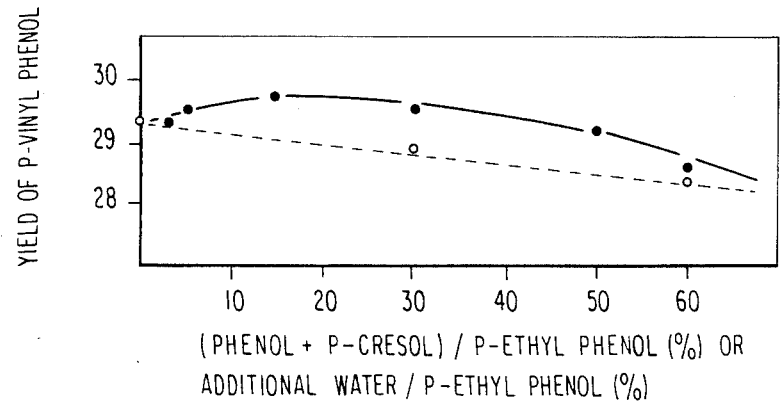
FIG. 1(c) illustrates the yield of p-vinyl phenol as obtained in Examples 1 to 4 and Comparative Examples 1 to 5.

The advantages of the present invention will be better understood by reference to FIG. 1 that illustrates the results of Examples 1 to 4 and Comparative Examples 1 to 5. In FIG. 1, the cumulative amount of phenol and p-cresol or the amount of additional water against p-ethyl phenol is shown on the x-axis, and the percent conversion from p-ethyl phenol (FIG. 1a), the selectivity for p-vinyl phenol (FIG. 1b) and the yield of p-vinyl phenol (FIG. 1c) are shown on the y-axis. The results of Examples 1 to 4 and Comparative Examples 2 and 3 wherein both phenol and p-cresol were added to p-ethyl phenol are plotted by solid dots, and those of Comparative Examples 1, 4 and 5 wherein neither compound was added are plotted by open dots.

EXAMPLE 5

Dehydrogenation of p-ethyl phenol was effected as in Example 1 except that 30 parts of phenol where added to 100 parts of the p-ethyl phenol. An oil phase and an aqueous phase were obtained in an amount of 140% and 132% of the p-ethyl phenol feed, respectively. The oil phase was composed of 21.1% of phenol, 1.2% of p-cresol, 20.3% of p-vinyl phenol, 0.1% of a low-molecular weight polymer of p-vinyl phenol, 0.5% of an unknown substance, 47.6% of unreacted p-ethyl phenol and 9.2% of water. The aqueous phase was composed of 0.8% of phenol, 0.1% of p-cresol, 0.4% of p-vinyl phenol, 0.5% of p-ethyl phenol and balance of water. Therefore, the percent conversion from p-ethyl phenol was 33.0%, the selectivity for p-vinyl phenol was 88.0%, and the yield of p-vinyl phenol was 29.0%.

EXAMPLE 6

Dehydrogenation of p-ethyl phenol was effected as in Example 1 except that 30 parts of p-cresol were added to 100 parts of the p-ethyl phenol. An oil phase and an aqueous phase were obtained in an amount of 139% and 133% of the p-ethyl phenol feed, respectively. The oil phase was composed of 1.1% of phenol, 21.6% of p-cresol, 20.5% of p-vinyl phenol, 0.1% of a low-molecular weight polymer of p-vinyl phenol, 0.5% of an unknown substance, 47.7% of unreacted p-ethyl phenol and 8.5% of water. The aqueous phase was composed of 0.1% of phenol, 0.4% of p-cresol, 0.3% of p-vinyl phenol, 0.5% of p-ethyl phenol and balance of water. Therefore, the percent conversion from p-ethyl phenol was 32.9%, the selectivity for p-vinyl phenol was 88.2%, and the yield of p-vinyl phenol was 29.0%.

COMPARATIVE EXAMPLE 6

Dehydrogenation of p-ethyl phenol was effected as in Example 1 except that the phenol and p-cresol were replaced by 30 parts of benzene to 100 parts of the p-ethyl phenol. An oil phase and an aqueous phase were obtained in an amount of 131% and 139% of the p-ethyl phenol feed, respectively. The oil phase was composed of 0.9% of phenol, 1.4% of p-cresol, 20.9% of p-vinyl phenol, 0.8% of a low-molecular weight polymer of p-vinyl phenol, 0.2% of an unknown substance, 50.5% of unreacted p-ethyl phenol, 21.5% of benzene and 3.8% of water. The aqueous phase was composed of 0.1% of phenol, 0.1% of p-cresol, 0.1% of p-vinyl phenol, 0.2% of p-ethyl phenol and balance of water. Therefore, the percent conversion from p-ethyl phenol was 33.5%, the selectivity for p-vinyl phenol was 82.1%, and the yield of p-vinyl phenol was 27.5%.

EXAMPLE 7

Dehydrogenation of p-ethyl phenol was effected as in Example 1 except that 10 parts of phenol and 20 parts of p-cresol were added to 100 parts of p-ethyl phenol and a tin oxide-barium oxide catalyst (the weight ratio of Sn to Ba is 90:10 as a metal) was used as a dehydrogenation catalyst. An oil phase and an aqueous phase were obtained in an amount of 138% and 134% of the p-ethyl phenol feed, respectively. The oil phase was composed of 7.1% of phenol, 14.6% of p-cresol, 22.4% of p-vinyl phenol, 0.4% of a low-molecular weight polymer of p-vinyl phenol, 0.1% of an unknown substance, 47.5% of unreacted p-ethyl phenol and 7.9% of water. The aqueous phase was composed of 0.3% of phenol, 0.3% of p-cresol, 0.4% of p-vinyl phenol, 0.5% of p-ethyl phenol and balance of water. Therefore, the percent conversion from p-ethyl phenol was 33.8%, the selectivity for p-vinyl phenol was 92.9%, and the yield of p-vinyl phenol was 31.4%.

COMPARATIVE EXAMPLE 7

Dehydrogenation of p-ethyl phenol was effected as in Example 1 except that neither phenol nor p-cresol was added to the p-ethyl phenol and the same tin oxide-barium oxide catalyst as in Example 7 was used as a dehydrogenation catalyst. An oil phase and an aqueous phase were obtained in an amount of 107% and 135% of the p-ethyl phenol feed, respectively. The oil phase was composed of 0.7% of phenol, 1.4% of p-cresol, 28.9% of p-vinyl phenol, 0.5% of a low-molecular weight polymer of p-vinyl phenol, 0.5% of an unknown substance, 59.5% of unreacted p-ethyl phenol and 8.5% of water. The aqueous phase was composed of 0.1% of phenol, 0.1% of p-cresol, 0.3% of p-vinyl phenol, 0.4% of p-ethyl phenol and balance of water. Therefore, the percent conversion from p-ethyl phenol was 36.0%, the selectivity for p-vinyl phenol was 86.9%, and the yield of p-vinyl phenol was 31.3%.

EXAMPLE 8

Dehydrogenation of p-ethyl phenol was effected as in Example 1 except that 10 parts of phenol and 20 parts of p-cresol were added to 100 parts of p-ethyl phenol and a chromium (III) oxide was used as a dehydrogenation catalyst. An oil phase and an aqueous phase were obtained in an amount of 139% and 134% of the p-ethyl phenol feed, respectively. The oil phase was composed of 7.1% of phenol, 14.7% of p-cresol, 19.8% of p-vinyl phenol, 0.3% of a low-molecular weight polymer of p-vinyl phenol, 0.2% of an unknown substance, 49.3% of unreacted p-ethyl phenol and 8.6% of water. The aqueous phase was composed of 0.4% of phenol, 0.3% of p-cresol, 0.4% of p-vinyl phenol, 0.4% of p-ethyl phenol and balance of water. Therefore, the percent conversion from p-ethyl phenol was 31.0%, the selectivity for p-vinyl phenol was 90.6%, and the yield of p-vinyl phenol was 28.1%.

COMPARATIVE EXAMPLE 8

Dehydrogenation of p-ethyl phenol was effected as in Example 1 except that neither phenol nor p-cresol was added to the p-ethyl phenol and the same chromium oxide as in Example 8 was used as a dehydrogenation catalyst. An oil phase and an aqueous phase were obtained in an amount of 107% and 135% of the p-ethyl phenol feed, respectively. The oil phase was composed of 1.2% of phenol, 2.2% of p-cresol, 25.7% of p-vinyl phenol, 0.6% of a low-molecular weight polymer of p-vinyl phenol, 0.6% of an unknown substance, 61.3% of unreacted p-ethyl phenol and 8.4% of water. The aqueous phase was composed of 0.1% of phenol, 0.1% of p-cresol, 0.3% of p-vinyl phenol, 0.4% of p-ethyl phenol and balance of water. Therefore, the percent conversion from p-ethyl phenol was 34.0%, the selectivity for p-vinyl phenol was 82.1%, and the yield of p-vinyl phenol was 27.9%.

While the invention has been described in detail and with reference to specific embodiments thereof, it will be apparent to one skilled in the art that various changes and modifications can be made therein without departing from the spirit and scope thereof.

What is claimed is:

1. A process for the production of p-vinyl phenol by dehydrogenation of p-ethyl phenol in a gaseous phase at a temperature of 400° to 700° C. in the presence of a catalyst capable of dehydrogenation and a diluent, wherein said dehydrogenation of p-ethyl phenol is effected in the presence of phenol and p-cresol in amounts such that the total amount of said two components falls in the range of 5 to 40% by weight based on the amount of p-ethyl phenol, and the ratio of the amount of said phenol to that of said p-cresol falls in the range of 1:0.5 to 1:5 by weight.

2. A process according to claim 1 wherein the phenol and p-cresol is present in an amount of 7 to 40 wt% of the amount of p-ethyl phenol.

3. A process according to claim 1 wherein when both phenol and p-cresol are present, the weight ratio thereof is 1:1 to 1:3.

4. A process according to claim 1 wherein the p-ethyl phenol is a pure form thereof and phenol and/or p-cresol is affirmatively added.

5. A process according to claim 1 wherein the p-ethyl phenol is a recycled product from the dehydrogenation step and at least part of the phenol and/or p-cresol is accounted for by the phenol and/or p-cresol that has been carried over from said dehydrogenation step.

6. A process according to claim 1 wherein the catalyst is selected from the group consisting of: (a) an iron oxide which is optionally supported on an alkaline earth metal oxide; (b) an oxide of at least one metal selected from the group consisting of vanadium, molybdenum, manganese, cobalt, nickel, copper, zinc, cadmium, antimony, tellurium and cerium, said oxide being optionally supported on an alkaline earth metal oxide; (c) chromium (III) oxide optionally combined with at least one metal oxide selected from the group consisting of zinc oxide, manganese oxide, titanium oxide and zirconium oxide, said chromium (III) oxide or its conbination with said other metal oxide being optionally supported on an inert carrier; (d) tin (IV) oxide optionally combined with metallic tin powder or at least one metal oxide selected from the group consisting of magnesium oxide, chromium (III) oxide, zinc oxide and manganese (IV) oxide, said tin (IV) oxide or its combination with metallic tin powder or said other metal oxide being optionally supported on an inert carrier; (e) titanium (IV) oxide optionally combined with at least one metal oxide selected from the group consisting of manganese oxide, iron oxide, copper oxide, zinc oxide, zirconium oxide, molybdenum oxide, tin oxide, antimony oxide, cerium oxide, lithium oxide, magnesium oxide, calcium oxide and barium oxide, said titanium (IV) oxide or its combination with another metal oxide being optionally supported on an inert carrier; and (f) an oxide containing both barium and tin which is optionally combined with at least one metal oxide selected from the group consisting of vanadium oxide, manganese oxide, iron oxide, copper oxide, zinc oxide, zirconium oxide, molybdenum oxide, antimony oxide, bismuth oxide and cerium oxide, said barium- and tin-containing oxide or its combination with said other metal oxide being optionally supported on an inert carrier.

7. A process according to claim 1 wherein the diluent is selected from the group consisting of water, benzene, toluene, xylene, low-boiling point petroleum fractions, carbon monoxide, carbon dioxide, nitrogen, helium, argon, and mixtures thereof.

8. A process according to claim 7 wherein the diluent is selected from the group consisting of water, benzene and toluene.

9. A process according to claim 1 wherein said dehydrogenation is conducted between 500° and 600° C.

10. A process as in claim 1 wherein the supply rate of p-ethyl phenol is between 0.1 and $5.0^{-hr}$ in terms of the liquid hourly space velocity (LHSV).

11. A process as in claim 1 wherein the supply rate of p-ethyl phenol is between 0.2 to $2.0^{-hr}$ in terms of the liquid hourly space velocity (LHSV).

* * * * *